United States Patent [19]

Campbell et al.

[11] Patent Number: 4,806,557
[45] Date of Patent: Feb. 21, 1989

[54] DIHYDROPYRIDINES AND USE THEREOF IN TREATING HYPERTENSION AND ISCHAEMIA

[75] Inventors: Simon F. Campbell, Kingsdown; Michael J. Humphrey, Sandwich; Alan Stobie, Hambrook, all of England

[73] Assignee: Pfizer Inc., New York, N.Y.

[21] Appl. No.: 187,116

[22] Filed: Apr. 28, 1988

[30] Foreign Application Priority Data

May 2, 1987 [GB] United Kingdom ................ 8710493

[51] Int. Cl.[4] ..................... A61K 31/44; C07D 211/90
[52] U.S. Cl. ...................................... 514/356; 546/321
[58] Field of Search ....................... 546/335, 337, 321; 514/357, 356

[56] References Cited

U.S. PATENT DOCUMENTS 4,447,613  5/1984  Henrick .............................. 546/335

OTHER PUBLICATIONS

K. G. Hofbauer et al., *J. Pharm. Exp. Therap.*, 232, 838 (1985).
H. M. N. W. Nievelstein et al., *J. Pharm. Exp. Therap.*, 235, 778 (1985).
V. J. Stella, *J. Med. Chem.*, 23, 1275 (1980).
S. D. J. Magnan et al., *J. Med. Chem.*, 25, 1018 (1982).
S. Wilk et al., *J. Pharm. Exp. Therap.*, 206, 227 (1978).
M. Orlowski et al., *J. Pharm. Exp. Therap.*, 212, 167 (1980).
J. F. M. Smits et al., *J. Pharm. Exp. Therap.*, 232 845 (1985).
F. N. Minard et al., *J. Chem. Pharmacology*, 29, 69 (1980).

*Primary Examiner*—Mary C. Lee
*Assistant Examiner*—Robert C. Whittenbaugh
*Attorney, Agent, or Firm*—Peter C. Richardson; J. Trevor Lumb; James M. McManus

[57] ABSTRACT

A compound of the formula:

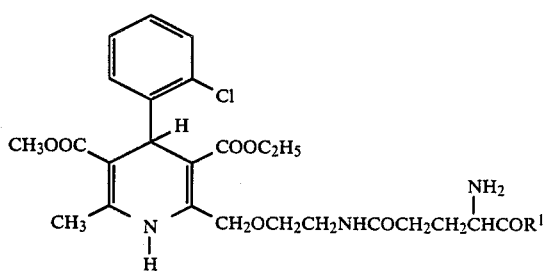

(I)

or a pharmaceutically acceptable salt thereof, wherein $R^1$ is amino, hydroxy, alkoxy, phenoxy or benzyloxy, useful in the treatment of hypertension, angina, renal impairment or acute renal failure.

6 Claims, No Drawings

DIHYDROPYRIDINES AND USE THEREOF IN TREATING HYPERTENSION AND ISCHAEMIA

BACKGROUND OF THE INVENTION

This invention relates to certain dihydropyridines which are pro-drugs of the calcium antagonist amlodipine, which is chemically known as 2-(2-aminoethoxymethyl)-4-(2-chlorophenyl)-3-ethoxycarbonyl-5-methoxycarbonyl-6-methyl-1,4-dihydropyridine (see EP-B-0089167), and to intermediates useful in the preparation of these pro-drugs.

Calcium antagonists reduce the movement of calcium into the cell and are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and, possibly, promotion of cell necrosis. Thus calcium antagonists are useful in the treatment or prevention of a variety of cardiac conditions, such as angina pectoris, cardiac arrythmias, heart attacks and cardiac hypertrophy. Calcium antagonists also have vasodilator activity since they can inhibit calcium influx in cells of vascular tissue and are thus also useful as antihypertensive agents and for the treatment of coronary vasospasm.

SUMMARY OF THE INVENTION

Thus the invention provides 1,4-dihydropyridine derivatives of the formula (I):

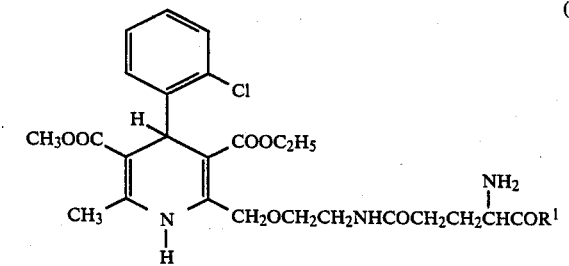

(I)

and their pharmaceutically acceptable salts, wherein $R^1$ is amino, hydroxy, alkoxy of one to six carbon atoms, phenyloxy or benzyloxy.

Preferred within this group of compounds is that wherein $R^1$ is hydroxy.

Also included as part of the present invention is a pharmaceutical composition comprising an antihypertensive or antiischaemic effective amount of a compound of formula I together with a pharmaceutically acceptable diluent or carrier.

The present invention is also directed to methods for treating hypertension and ischaemia in mammals which comprises the step of administering to said mammals an antihypertensive or antischaemic effective amount of a compound of formula I.

Also included within the scope of the invention are the synthetic intermediates of the formula:

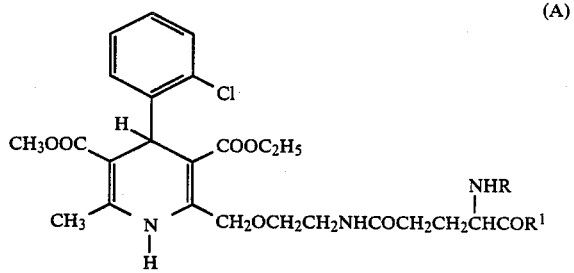

(A)

where R is an amino-protecting group, preferably benzyloxycarbonyl or t-butoxycarbonyl, and $R^1$ is as defined for formula (I).

DETAILED DESCRIPTION OF THE INVENTION

The compounds of the formula (I) are all preparable by the removal of the amino-protecting group from the corresponding N-protected compounds of the formula (A). As stated above, the preferred protecting groups are benzyloxycarbonyl and t-butoxycarbonyl. These can be removed by conventional methods. For example, the benzyloxycarbonyl group is typically removed by the hydrogenolysis of the N-protected 1,4-dihydropyridine in a suitable solvent, e.g. 10% aqueous ethanol, under an atmosphere of hydrogen at, say, 15–30 p.s.i. (103.4–206.8 kPa) at about room temperature and in the presence of a 5% palladium on carbon catalyst. The t-butoxycarbonyl group is typically removed by treatment with an acid, e.g. by treatment of the N-protected 1,4-dihydropyridine at about room temperature in a suitable organic solvent, e.g. dichloromethane, with gaseous hydrogen chloride.

The N-protected starting materials can be prepared by conventional techniques which are illustrated schematically as follows:

Amlodipine + HOOCCH$_2$CH$_2$CHCOOR$^4$ with NH.R$^3$ (a) ↓

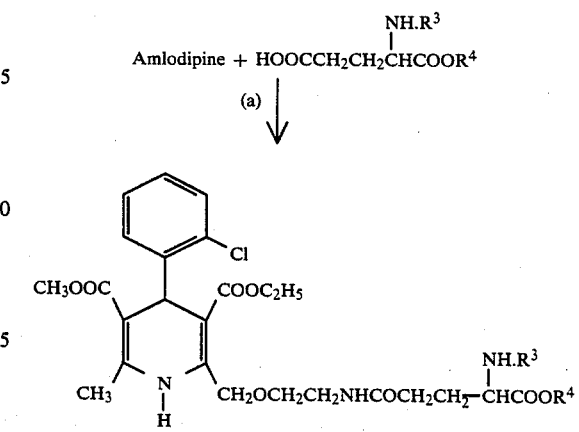

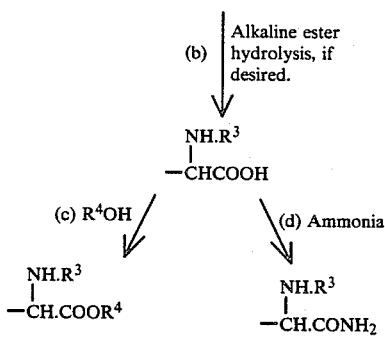

In the above, $R^3$ is an amino-protecting group and $R^4$ is $C_1$–$C_6$ alkyl, phenyl or benzyl.

The coupling reactions of steps (a) and (c) are typically carried out by forming an "activated" derivative of the acid in situ as will be known to those skilled in the art, typically by reacting the acid with 1-hydroxybenzotriazole, 4-dimethylaminopyridine or N-hydroxysuccinimide in the presence of N,N'-dicyclohexylcarbodiimide or 1-(3-dimethylaminopropyl)-3-ethylcarbodiimide at about room temperature in a suitable organic solvent such as dichloromethane. The "activated" derivative is then reacted with amlodipine in step (a) or the alcohol in step (c). Since 1-(3-dimethylaminopropyl)-3-ethylcarbodiimide is most readily available as the hydrochloride salt, it is typically used in the process in salt form but in the presence of a base such as triethylamine.

Similarly, the amides are typically formed in step (d) by reacting the acid with, e.g., carbonyldiimidazole so as to form an "activated" derivative of the acid (i.e. an acyl imidazole), followed by reaction of the "activated" derivative with ammonia. These reactions are usually carried out at between 0° and room temperature in an appropriate organic solvent, e.g. tetrahydrofuran, and the ammonia is typically used in gaseous form.

The alkaline hydrolysis of step (b) is preferably carried out by reacting the ester in an organic solvent such as dioxan with aqueous sodium hydroxide at about room temperature.

The N-protected amino-acid starting materials are either commercially available (especially in the S-form) or are preparable by conventional techniques such as those illustrated in the following experimental section.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate, benzenesulphonate and p-toluenesulphonate salts.

The compounds of the formula (I) in which $R^1$ is hydroxy also form metal salts. The alkali metal salts, and especially the sodium and potassium salts, are preferred.

All the salts can be prepared conventionally.

When $R^1$ is hydroxy, the compounds of the formula (I) may exist in zwitterionic form and such forms are also within the scope of this invention.

The compounds of the formula (I) have two chiral centres and the invention includes both the resolved and unresolved forms. For synthetic convenience, it is preferred to use amlodipine in its R/S form and the N-protected amino-acid in its S-form.

The effect of the compounds of the formula (I) on coronary blood flow and urinary excretion of sodium in anaesthetised dogs can be measured as follows:

Dogs are anaesthetised and catheters inserted into blood vessels for the measurement of blood pressure, heart rate and coronary blood flow. Urine is collected from catheters inserted into both ureters and the concentration of sodium determined. The animals receive a continuous intravenous infusion of 0.9% sodium chloride in water at a rate of 10 ml/kg/h. The effect of the test compound is assessed by observing changes in coronary blood flow and changes in urinary excretion of sodium following intravenous administration of the test compound.

The antihypertensive activity of the compounds can be measured by the following techniques:

The antihypertensive activity of the test compound administered by intravenous injection is determined by measuring the fall in the blood pressure of renally hypertensive conscious dogs. In addition, the compounds can also be administered orally to spontaneously hypertensive rats.

The natriuretic activity of the compounds can be assessed in conscious dogs as follows:

Dogs are fasted for 24 hours before the experiment. Urine is collected from the dogs over three 30 minute time periods to determine the baseline excretion rate of sodium. A dose of 3 mEq/kg sodium chloride (as a 0.9% solution in water) is administered orally and further urine samples are collected for 3 hours. The recovery of the oral sodium load from the urine is calculated as the total recovery in 3 hours minus the baseline sodium excretion. A compound is deemed to have natriuretic activity if its prior administration, for example by intravenous injection, causes a significant increase in urinary sodium excretion over the 3 hour test period.

The compounds of formula (I) are metabolised to amlodipine and therefore display calcium antagonist activity in vivo after oral or parenteral administration. For example, following intravenous administration to dogs, these compounds lower coronary and systemic vascular resistance and are thus useful for the treatment of angina and hypertension. In addition, at least when the compounds of the formula (I) are administered parenterally, a pronounced natriuretic effect is also observed, which is believed to be due to preferential conversion of these pro-drugs to amlodipine in the kidney. These compounds are therefore useful (at least when given parenterally) in the treatment of patients with renal impairment, acute renal failure and in pre-operative care prior to surgery.

For human use, the compounds of the formula (I) can be administered alone, but will generally be administered in admixture with a pharmaceutical carrier selected with regard to the intended route of administration and standard pharmaceutical practice. For example, they may be administered orally or sublingually in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously, or administered via a transdermal device.

For administration to man in the curative or prophylactic treatment of cardiac conditions and hypertension, oral dosages of the compounds will generally be in the range of from 2–200 mg daily for an average adult patient (70 kg). Thus for a typical adult patient, individual tablets or capsules may contain from 1 to 100 mg of active compound, in a suitable pharmaceutically acceptable vehicle or carrier. Dosages for parenteral administration would typically be within the range 1 to 10 mg per single dose as required.

In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For parenteral administration, the compounds are best used in the form of a sterile aqueous solution which may contain other substances, for example, enough salts or glucose to make the solution isotonic with blood.

The following Examples, in which all temperatures are in °C., illustrate the invention:

EXAMPLE 1

2-[2-(-(S)-4-Amino-4-methoxycarbonylbutanamido)ethoxymethyl]-4-(2-chlorophenyl)-3-ethoxycarbonyl-5-methoxycarbonyl-6-methyl-1,4-dihydropyridine A solution of 2-[2-(-(S)-4-benzyloxycarbonylamino-4-methoxycarbonylbutanamido)ethoxymethyl]-4-(2-chlorophenyl)-3-ethoxycarbonyl-5-mehoxycarbonyl-6-methyl-1,4-dihydropyridine (0.89 g) in 10% aqueous ethanol (22 ml) was stirred for 2 hours under an atmosphere of hydrogen [103.4 kPa (15 p.s.i.)] at room temperature in the presence of 5% palladium on carbon (90 mg). The mixture was filtered and evaporated and the residue purified by chromatography on silica using dichloromethane plus 0→4% methanol as the eluant. Appropriate fractions were combined and evaporated to leave the title compound (0.38 g) as an oil.

N.m.r. (300 mHz, CDCl$_3$): δ=1.20 (3H, t, 3-CO$_2$CH$_2$CH$_3$); 1.8–2.6 (4H, m, 2×CH$_2$); 2.4 (3h, s, 6-CH$_3$); 3.4–3.8 (10H, m, 2×CH$_2$, 3-CO$_2$CH$_3$, 5-CO$_2$CH$_3$); 4.1 (2H, m, 3-CO$_2$CH$_2$CH$_3$); 4.8 (2H, m, 2-CH$_2$—O—); 5.4 (1H, s, 4-H); 7.0–7.6 (4H, m, ArH).

Mass spectra m/e (M+H)$^+$=552.

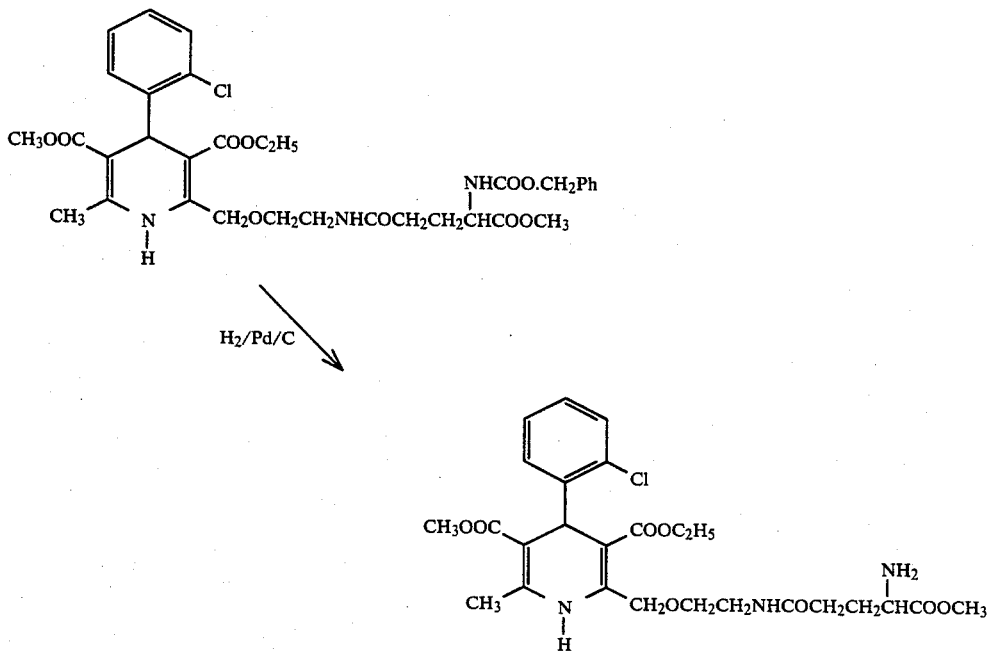

EXAMPLE 2

2-[2-(-(S)-4-Amino-4-carboxybutanamido)ethoxymethyl]-4-(2-chlorophenyl)-3-ethoxycarbonyl-5-methoxycarbonyl-6-methyl-1,4-dihydropyridine

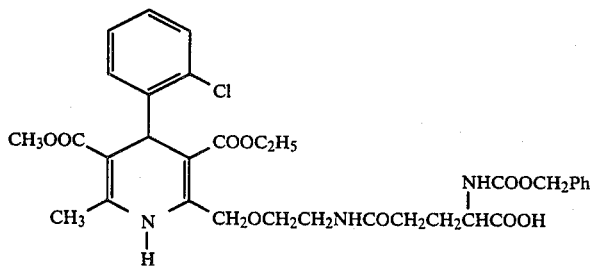

H$_2$/Pd/C

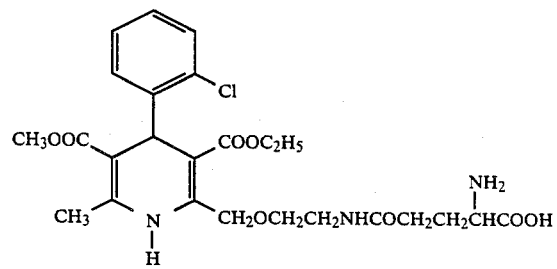

A solution of 2-[2-(-(S)-4-benzyloxycarbonylamino-4-carboxybutanamido)ethoxymethyl]-4-(2-chlorophenyl)-3-ethoxycarbonyl-5-methoxycarbonyl-6-methyl-1,4-dihydropyridine (0.97 g) in 10% aqueous ethanol (22 ml) was stirred for 2 hours under an atmosphere of hydrogen [103.4 kPa (15 p.s.i.)] at room temperature in the presence of 5% palladium on carbon (97 mg). The mixture was filtered and evaporated to leave the title compound as an amorphous solid, (0.7 g).

Analysis %: Found: C,54.01; H,6.16; N,7.56; C$_{25}$H$_{32}$ClN$_3$O$_8$.H$_2$O requires: C,54.07; H,5.87; N,7.62.

EXAMPLE 3

2-[2-(-(S)-4-Amino-4-ethoxycarbonylbutanamido)ethoxymethyl]-4-(2-chlorophenyl)-3-ethoxycarbonyl-5-methoxycarbonyl-6-methyl-1,4-dihydropyridine

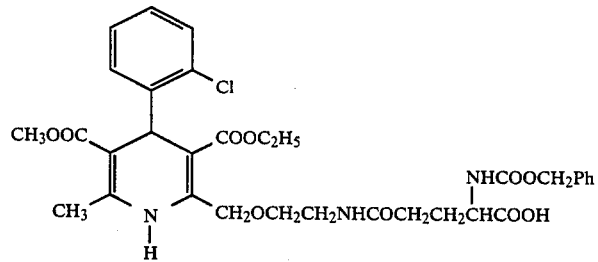

(i) EtOH/DCCD
(ii) H$_2$/Pd/C

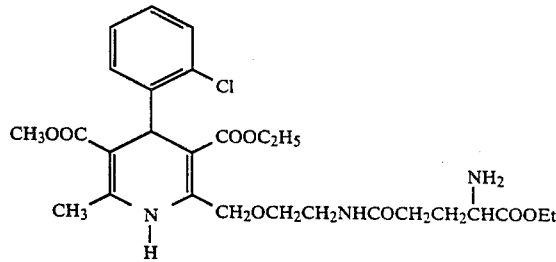

A mixture of 2-[2-(-(S)-4-benzyloxycarbonylamino-4-carboxybutanamido)ethoxymethyl]-4-(2-chlorophenyl)-3-ethoxycarbonyl-5-methoxycarbonyl-6-methyl-1,4-dihydropyridine (1.0 g), ethanol (0.27 g), N,N'- dicyclohexylcarbodiimide ("DCCD") (0.34 g) and 4-dimethylaminopyridine (50 mg) was stirred in dichloromethane (10 ml) at room temperature for 18 hours. The resulting N,N'-dicyclohexylurea was then removed by filtration and the filtrate evaporated. The residue was purified by chromatography on silica using dichloromethane plus 0→2% methanol as the eluant. Appropriate fractions were combined and evaporated to give 2-[2-(-(S)-4-benzyloxycarbonylamino-4-ethoxycarbonylbutanamido)ethoxymethyl]-4-(2-chlorophenyl)-3-ethoxycarbonyl-5-methoxycarbonyl-6-methyl-1,4-dihydropyridine (0.85 g) as an essentially pure oil.

The above oil in 10% aqueous ethanol (22 ml) containing 5% Pd on C (0.085 g) was hydrogenated and purified as described in Example 1 above to give the title compound (0.55 g) as an oil.

N.m.r. (300 mHz, CDCl$_3$): δ=1.20 (3H, t, 3-CO$_2$CH$_2$CH$_3$); 1.25 (3H, t, CO$_2$CH$_2$CH$_3$); 1.8-2.6 (4H, m, 2×CH$_2$); 2.4 (3H, s, 6-CH$_3$); 3.4-3.8 (7H, m, 2×CH$_2$, 5-CO$_2$CH$_3$); 4.1 (2H, m, 3-CO$_2$CH$_2$CH$_3$); 4.2 (2H, q, CO$_2$CH$_2$CH$_3$); 4.7 (2H, m, 2-CH$_2$O); 5.4 (1H, s, 4-H); 7.0-7.6 (4H, m, ArH).

Mass spectra: m/e (M+H)$^+$ =566.

EXAMPLE 4

2-[2-(-(S)-4-Amino-4-carbamoylbutanamido)ethoxymethyl]-4-(2-chlorophenyl)-3-ethoxycarbonyl-5-methoxycarbonyl-6-methyl-1,4-dihydropyridine temperature, the mixture was stirred for 2 hours and then treated with gaseous ammonia for ½ hour. The mixture was then evaporated and the residue partitioned between 10% aqueous sodium carbonate solution and ethyl acetate. The aqueous layer was extracted with two further portions of ethyl acetate. The organic extracts were combined, washed with brine, dried over magnesium sulphate and evaporated. The residue was purified by chromatography on silica, eluting with dichloromethane plus 0→5% methanol. Appropriate fractions were combined and evaporated to give 2-[2-(-(S)-4-benzyloxycarbonylamino-4-carbamoylbutanamido)-ethoxymethyl]-4-(2-chlorophenyl)-3-ethoxycarbonyl-5-methoxycarbonyl-6-methyl-1,4-dihydropyridine (0.84 g) as an essentially pure oil.

The above oil in 10% aqueous ethanol (22 ml) containing 5% Pd on C (0.085 g) was hydrogenated as described in Example 1. Purification was by chromatography on silica using dichloromethane containing 1% ammonia and 2→10% methanol as the eluant. The title compound (0.52 g) was obtained as an oil.

N.m.r. (300 mHz, CDCl$_3$): δ=1.2 (3H, t, 3-CO$_2$CH$_2$CH$_3$); 1.6-2.6 (4H, m, 2×CH$_2$); 2.4 (3H, s, 6-CH$_3$); 3.4-3.8 (7H, m, 2×CH$_2$, 5-CO$_2$CH$_3$); 4.1 (2H, m, 3-CO$_2$CH$_2$CH$_3$); 4.7 (2H, m, 2-CH$_2$O); 5.3 (1H, s, 4-H); 5.5 (1H, br s, NH); 6.8 (1H, br s, NH); 7.0-7.5 (4H, m, ArH).

Mass spectra: m/e (M+H)$^+$ =537.

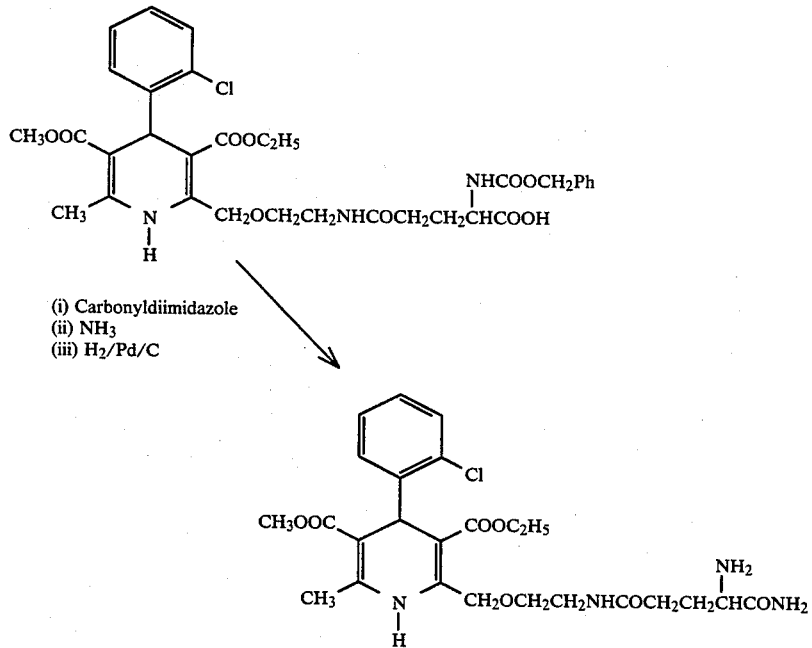

Carbonyldiimidazole (0.36 g) was added to an ice cold solution of 2-[2-(-(S)-4-benzyloxycarbonylamino-4-carboxybutanamido)ethoxymethyl]-4-(2-chlorophenyl)-3-ethoxycarbonyl-5-methoxycarbonyl-6-methyl-1,4-dihydropyridine (1.0 g) in tetrahydrofuran (20 ml). After allowing the reaction mixture to reach room

EXAMPLE 5

2-[2-(-(S)-4-Amino-4-n-pentoxycarbonylbutanamido)ethoxymethyl]-4-(2-chlorophenyl)-3-ethoxycarbonyl-5-methoxycarbonyl-6-methyl-1,4-dihydropyridine magnesium sulphate and evaporated. The residue was purified by chromatography on silica eluting with dichloromethane containing gradually increasing amounts (0→2%) of methanol. Appropriate fractions were combined and evaporated to give 2-[2-(-(S)-4-t-

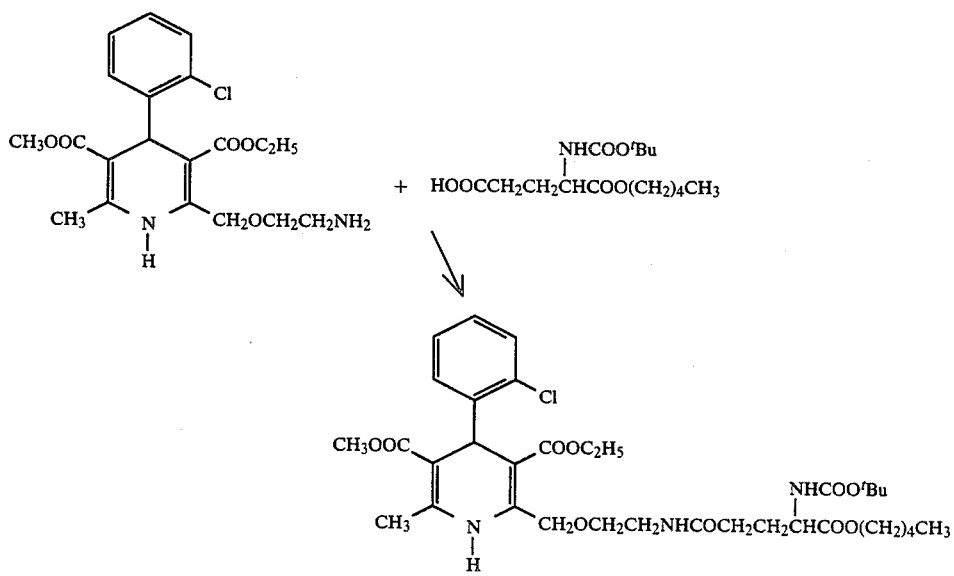

A mixture of 2-(2-aminoethoxymethyl)-4-(2-chlorophenyl)-3-ethoxycarbonyl-5-methoxycarbonyl-6-methyl-1,4-dihydropyridine ("amlodipine") (3.93 g), (S)-4-(t-butoxycarbonylamino)-4-n-pentoxycarbonylbutanoic acid (3.36 g), 1-(3-dimethylaminopropyl)-3-ethylcarbodiimide hydrochloride (2.03 g), 1-hydroxybenzotriazole (1.43 g) and triethylamine (1.07 g) was stirred in dichloromethane (60 ml) at room temperature for 18 hours. After evaporation the residue was partitioned between ethyl acetate and saturated aqueous sodium bicarbonate solution. The aqueous layer was extracted with three further portions of ethyl acetate. The organic extracts were combined, washed with brine, dried over butoxycarbonylamino-4-n-pentoxycarbonylbutanamido)ethoxymethyl]-4-(2-chlorophenyl)-2-ethoxycarbonyl-5-methoxycarbonyl-6-methyl-1,4-dihydropyridine (4.7 g) as an essentially pure oil.

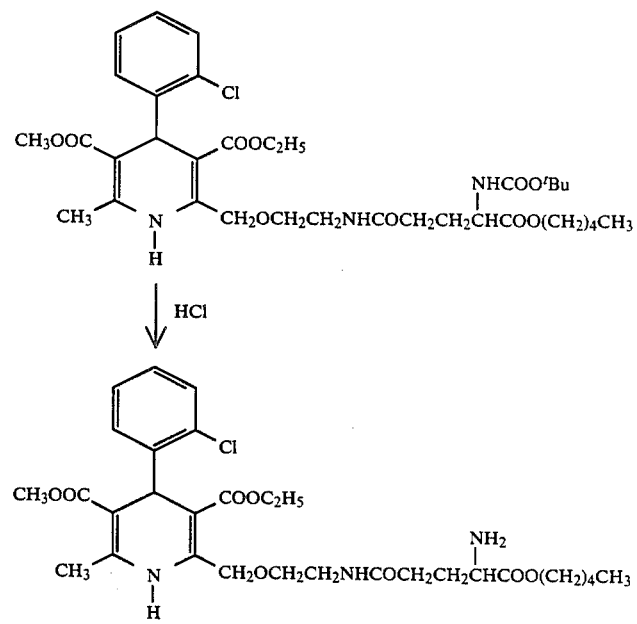

The oil from part (a) above (2.3 g) in dichlormethane (75 ml.) was treated at room temperature with gaseous hydrogen chloride for 2 hours. After air-induced removal of excess hydrogen chloride, the mixture was evaporated and the residue partitioned between ethyl acetate and saturated aqueous sodium bicarbonate solution. The organic layer was washed with brine, dried over magnesium sulphate and evaporated. The residue was purified by chromatography on silica using dichloromethane containing 0→4% methanol as the eluant. Appropriate fractions were combined and evaporated to give the title compound (0.5 g) as an oil.

N.m.r. (300 mHz, CDCl$_3$): δ=0.9 (3H, t, —O(CH$_2$)$_4$CH$_3$); 1.2 (3H, t, 3-CO$_2$CH$_2$CH$_3$); 1.3 (4H, m, —CO$_2$CH$_2$CH$_2$CH$_2$CH$_2$CH$_3$); 1.5–2.5 (6H, m, 3×CH$_2$); 2.4 (3H, s, 6-CH$_3$); 3.2–3.7 (7H, m, 2-CH$_2$OCH$_2$CH$_2$, 5-CO$_2$CH$_3$); 4.1 (4H, m, —CO$_2$CH$_2$C$_4$H$_9$, 3-CO$_2$CH$_2$CH$_3$); 4.7 (2H, m, 2-CH$_2$O); 5.4 (1H, s, 4-H); 7.0–7.6 (4H, m, ArH).

Mass spectra: m/e (M+H)$^+$=608.

EXAMPLE 6

2-[2-(-(S)-4-Amino-4-benzyloxycarbonylbutanamido)ethoxymethyl]-4-(2-chlorophenyl)-3-ethoxycarbonyl-5-methoxycarbonyl-6-methyl-1,4-dihydropyridine 3-ethylcarbodiimide hydrochloride (0.57 g), 1-hydroxybenzotriazole (0.40 g) and triethylamine (0.30 g) according to method of part (a) of Example 5 followed by treatment of the resulting intermediate in dichloromethane with gaseous hydrogen chloride according to the method of part (b).

N.m.r. (300 mHz, CDCl$_3$): δ=1.2 (3H, t, 3-CO$_2$CH$_2$CH$_3$); 1.6–2.6 (4H, m, 2×CH$_2$); 2.4 (3H, s, 6-CH$_3$); 3.3–3.8 (7H, m, 2-CH$_2$OCH$_2$CH$_2$, 5-CO$_2$LCH$_3$); 4.0 (2H, q, 3-CO$_2$CH$_2$CH$_3$); 4.7 (2H, m, 2-CH$_2$O); 5.1 (2H, s, CH$_2$Ph); 5.4 (1H, s, 4-H); 7.0–7.4 (9H, m, ArH).

Mass spectra: m/e (M+H)$^+$=628.

The following Preparations, in which all temperatures are in °C., illustrate the preparation of certain of the starting materials used in the previous Examples:

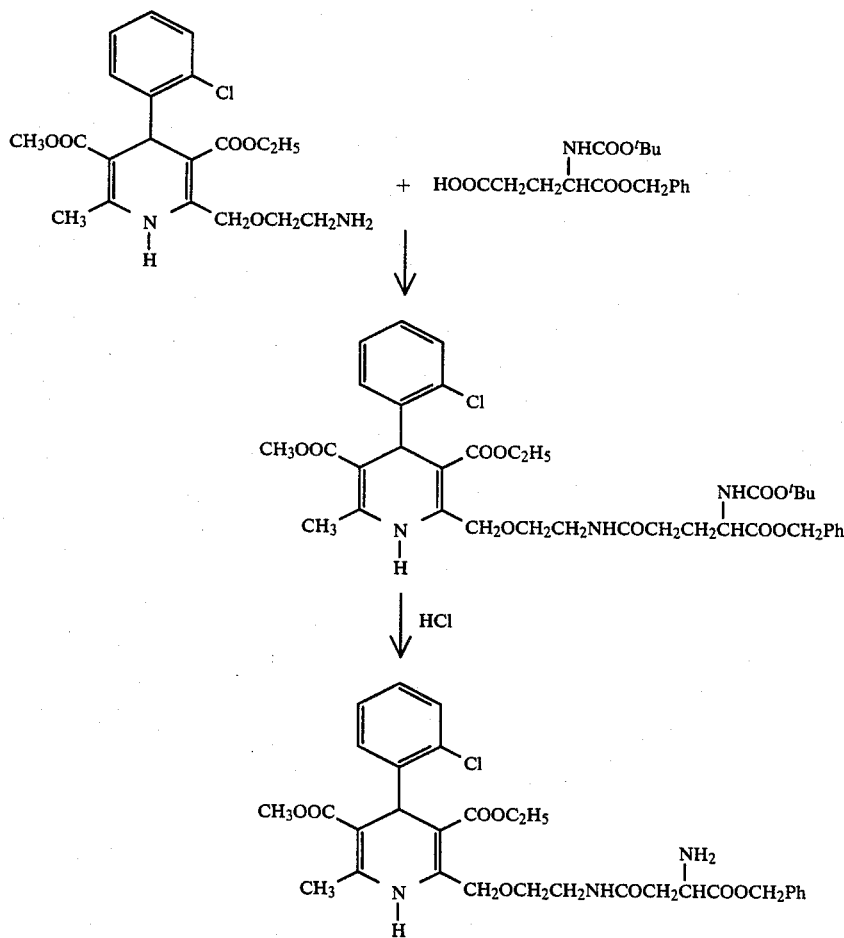

The title compound (0.29 g) was prepared as an oil by the reaction of amlodipine (1.1 g), (S)-4-benzyloxycarbonyl-4-t-butoxycarbonylaminobutanoic acid (1.0 g) (commercially available), 1-(3-dimethylaminopropyl)-

Preparation 1

2-[2-(-(S)-4-Benzyloxycarbonylamino-4-methoxycarbonylbutanamido)ethoxymethyl]-4-(2-chlorophenyl)-3-ethoxycarbonyl-5-methoxycarbonyl-6-methyl-1,4-dihydropyridine

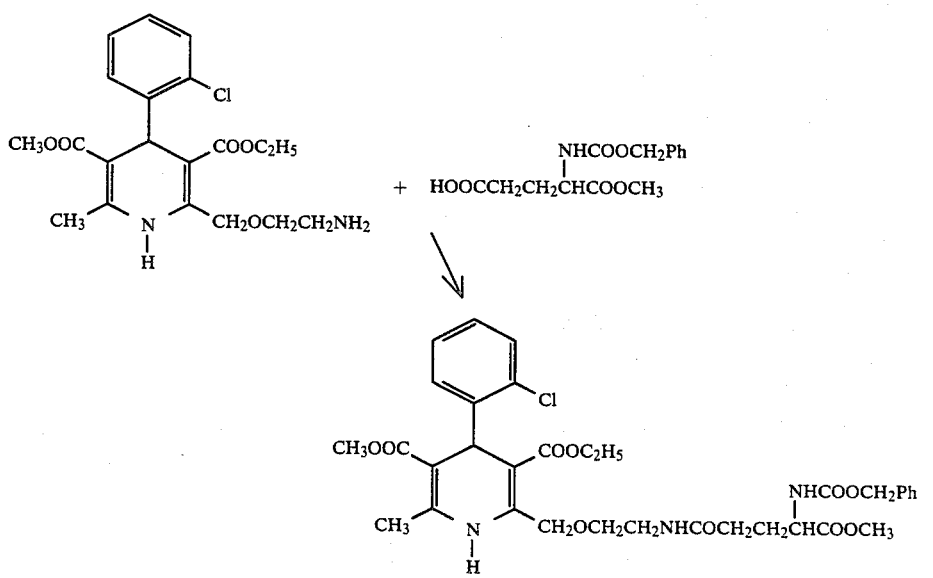

A mixture of 2-[2-aminoethoxymethyl]-4-(2-chlorophenyl)-3-ethoxycarbonyl-5-methoxycarbonyl-6-methyl-1,4-dihydropyridine (1.61 g), ("amlodipine"), (S)-4-benzyloxycarbonylamino-4-methoxycarbonylbutanoic acid (1.28 g) [see G. H. L. Nefkens and J. F. Nivard, Rec. Trav. Chim. Pays Bas, 199, 83, 1964], 1-(3-dimethylaminopropyl)-3-ethylcarbodiimide hydrochloride (0.83 g), 1-hydroxybenzotriazole (0.59 g) and triethylamine (0.44 g) in dichloromethane (25 ml) were reacted together as described in Example 5 part (a) to give the title compound (2.0 g) as an essentially pure solid foam which was used directly in Example 1 and Preparation 2 without further purification.

Preparation 2

2-[2-(-(S)-4-Benzyloxycarbonylamino-4-carboxybutanamido)ethoxymethyl]-4-(2-chlorophenyl)-3-ethoxycarbonyl-5-methoxycarbonyl-6-methyl-1,4-dihydropyridine

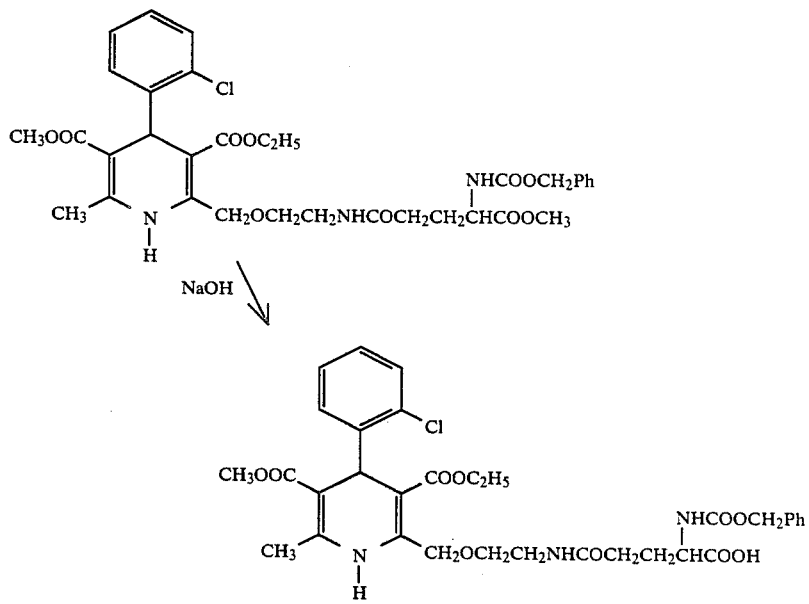

1M Aqueous sodium hydroxide (8.75 ml) was added to a solution of the product of Preparation 1 above (2.0 g) in dioxan (18 ml). After 2 hours at room temperature the mixture was evaporated and the residue partitioned between ethyl acetate and 1M hydrochloric acid. The organic layer was separated, dried over magnesium sulphate and evaporated. The residue was purified by column chromatography using dichloromethane containing ammonia (1%) and increasing amounts of methanol (10→15%) as the eluant. Appropriate fractions were combined and evaporaed to give the title compound (0.97 g) as a foam which was used directly in Examples 2, 3 and 4 without further purification.

Preparation 3

(S)-4-t-Butoxycarbonylamino-4-pentoxycarbonyl-butanoic acid

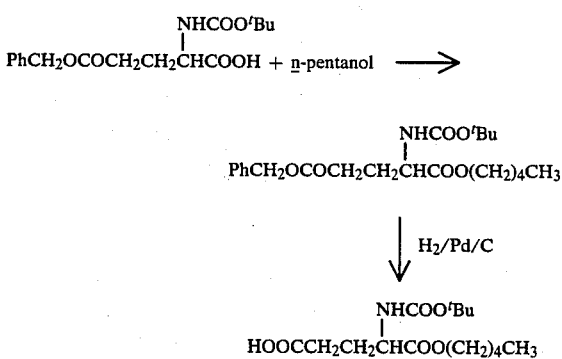

A mixture of (S)-benzyl 4-t-butoxycarbonylamino-4-carboxybutanoate (5 g) (commercially available), N,N'-dicyclohexylcarbodiimide (3.35 g), 4-dimethylaminopyridine (150 mg) and n-pentanol (5.2 g) was stirred in dichloromethane (30 ml) for 18 hours. The resulting N,N'-dicyclohexylurea was removed by filtration and the filtrate evaporated. The residue was dissolved in hexane, filtered and the filtrate evaporated to give (S)-benzyl 4-t-butoxycarbonylamino-4-pentoxycarbonylbutanoate (6 g) as an essentially pure oil.

This oil (4.1 g) in 10% aqueous ethanol (90 ml) containing 5% Pd on C (0.41 g) was hydrogenated as described in Example 1 above to give the title compound (3.36 g) as an essentially pure oil which was used directly in Example 5.

We claim:

1. A compound of the formula

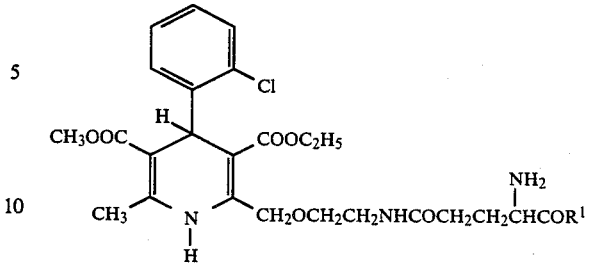

or a pharmaceutically acceptable salt thereof, wherein $R^1$ is amino, alkoxy of one to six carbon atoms, hydroxy, phenoxy or benzyloxy.

2. The compound of claim 1, wherein $R^1$ is hydroxy.

3. A pharmaceutical composition comprising an antihypertensive or antiischaemic effective amount of a compound according to claim 1 together with a pharmaceutically acceptable diluent or carrier.

4. A method of treating hypertension in a mammal comprising the step of administering to said mammal an antihypertensive effective amount of a compound according to claim 1.

5. A method of treating ischaemia in a mammal comprising the step of administering to said mammal an antiischaemic effective amount of a compound according to claim 1.

6. A compound of the formula

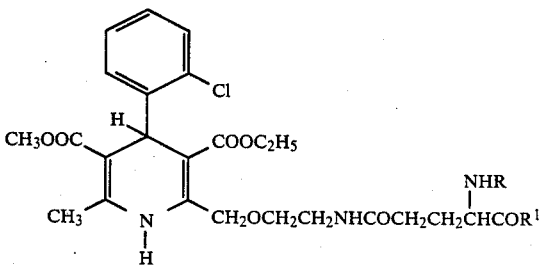

wherein R is benzyloxycarbonyl or t-butoxycarbonyl and $R^1$ is amino, alkoxy of one to six carbon atoms, hydroxy, phenoxy or benzyloxy.

* * * * *